United States Patent [19]

Marquis et al.

[11] Patent Number: 4,650,886

[45] Date of Patent: Mar. 17, 1987

[54] SYNTHESIS OF AMMONIUM MOLYBDATE/ALKANOL COMPLEXES

[75] Inventors: Edward T. Marquis, Austin; John R. Sanderson, Leander; Kenneth P. Keating, Georgetown; William A. Smith, Austin, all of Tex.

[73] Assignee: Texaco Inc., White Plains, N.Y.

[21] Appl. No.: 804,131

[22] Filed: Dec. 6, 1985

Related U.S. Application Data

[63] Continuation-in-part of Ser. No. 687,710, Dec. 31, 1984, abandoned.

[51] Int. Cl.$^4$ ............................................. C07F 11/00
[52] U.S. Cl. ..................................... 556/57; 502/171; 549/529
[58] Field of Search ........................................... 556/57

[56] References Cited

U.S. PATENT DOCUMENTS

| | | | |
|---|---|---|---|
| 2,795,552 | 6/1957 | Abbott et al. | 556/57 X |
| 3,121,059 | 2/1964 | De Young et al. | 556/61 X |
| 3,285,942 | 11/1966 | Price et al. | 556/57 |
| 3,480,563 | 11/1969 | Bonetti et al. | 556/57 X |
| 3,668,227 | 6/1972 | Mattucci et al. | 556/57 |
| 3,931,044 | 1/1976 | Maurin | 549/529 X |
| 3,956,180 | 5/1976 | Cavitt | 549/533 |
| 3,991,090 | 11/1976 | Hagstrom et al. | 556/57 |
| 4,009,122 | 2/1977 | Lines et al. | 556/57 X |
| 4,192,757 | 3/1980 | Brewster | 556/57 X |

*Primary Examiner*—Helen M. S. Sneed
*Attorney, Agent, or Firm*—Jack H. Park; Kenneth R. Priem

[57] ABSTRACT

Storage stable solutions of molybdenum/alkanol complexes in the alkanol are prepared by reacting an ammonium molybdate with an amount of a straight chain or branched chain $C_6$–$C_{13}$ alkanol, within the range of about 7 to about 20 moles of alkanol per gram atom of molybdenum sufficient to form a storage stable molybdenum/alkanol complex. The complex-forming reaction is initiated in the presence of about 1 to about 4 moles of added water per gram atom of molybdenum and is conducted at a temperature of about 120° to about 190° C. for a period of time, normally about 3 to about 8 hours, sufficient to substantially completely remove ammonia and water to provide a liquid reaction product comprising said solution of molybdenum/alkanol complex dissolved in unreacted alkanol and containing about 0.001 to about 0.1 wt. % of water. The reaction product is filtered to provide a clarified storage stable solution of the molybdenum/alkanol complex.

10 Claims, No Drawings

SYNTHESIS OF AMMONIUM MOLYBDATE/ALKANOL COMPLEXES

CROSS-REFERENCE TO RELATED APPLICATION

This application is a continuation-in-part of copending application Ser. No. 06/687,710 filed Dec. 31, 1984 and entitled "Improved Synthesis of Molybdenum/Alcohol Complexes Useful as Epoxidation Catalysts" now abandoned.

BACKGROUND OF THE INVENTION

1. Field of the Invention

The invention relates to a method for making molybdenum complexes and more particularly relates to a method for making molybdenum complexes useful as olefin epoxidation catalysts from an alkanol and an ammonium molybdate.

2. Other Related Methods in the Field

The epoxidation of olefins to give various epoxide compounds has long been an area of study by those skilled in the art. It is well known that the reactivities of the various olefins differ with the number of substituents on the carbon atoms involved in the double bond. Ethylene itself has the lowest relative rate of epoxidation, with propylene and other alpha olefins being the next slowest. Compounds of the formula $R_2C=CR_2$, where R simply represents alkyl or other substituents, may be epoxidized fastest. Thus, the more substituents on the double bond carbons, the easier it is to epoxidize across that bond.

The production of ethylene oxide from ethylene has long been known to be accomplished by reaction with molecular oxygen over a silver catalyst. Numerous patents have issued on various silver-catalyzed processes for the production of ethylene oxide. Unfortunately, the silver catalyst route will not work for olefins other than ethylene. For a long time the commercial production of propylene oxide could only be accomplished via the cumbersome chlorohydrin process.

A commercial process for the manufacture of substituted epoxides from alpha olefins such as propylene was not discovered until John Kollar's work in the 1960s. His U.S. Pat. No. 3,351,635 taught that an organic epoxide compound could be made by reacting an alpha olefin with an organic hydroperoxide in the presence of a molybdenum, tungsten, titanium, columbium, tantalum, rhenium, selenium, chromium, zirconium, tellurium or uranium catalyst. Kollar's U.S. Pat. No. 3,350,422 teaches a similar process using a soluble vanadium catalyst.

However, even though Kollar's work has been recognized as extremely important in the development of a commercial propylene oxide process that did not depend on the chlorohydrin route, it has been recognized that Kollar's catalytic route (in which molybdenum is the preferred catalyst) has a number of problems. For example, if t-butyl hydroperoxide is used as the peroxide, large quantities of t-butyl alcohol corresponding to the peroxide are formed and the t-butyl alcohol that is recovered must be of marketable quantity. An especially troublesome class of by-products are the propylene oligomers. If propylene is used, various propylene dimers, sometimes called hexenes, are separated from the propylene oxide only with great difficulty. In addition, the molybdenum catalyst may not be stable or the recovery of the catalyst for recycle may be poor.

Various avenues of investigation have been explored in attempts to improve on the molybdenum-catalyzed epoxidation of propylens. One technique was to try to improve on the catalyst itself. Patents which cover the preparation of various molybdenum epoxidation catalysts include U.S. Pat. No. 3,362,972 to Kollar. There a hydrocarbon soluble salt of molybdenum or vanadium may be made by heating a molybdenum compound in which molybdenum has a valence of $+6$, or a vanadium compound in which vanadium has a valence of $+5$, with a carboxylic acid of from 4 to 50 carbon atoms having at least 4 carbon atoms per carboxylic group. U.S. Pat. No. 3,578,690 to Becker discloses that molybdenum acid salts may be made by directly reacting a carboxylic acid with a molybdenum compound while removing the water that is formed.

The reaction of molybdenum trioxide with monohydric saturated alcohols having 4 to 22 carbon atoms or with a mono- or polyalkylene glycol monoalkyl ether or mixtures thereof to make olefin epoxidation catalysts is described in U.S. Pat. No. 3,480,563 to Bonetti, et al. These catalysts have only 0.07 to 0.93% molybdenum, which is a molybdenum content too low for maximum economy in commercial use.

In U.S. Pat. No. 4,434,975 to ARCO, investigators found that molybdenum catalysts could be made from saturated alcohols or glycols having one to four carbon atoms, such as ethylene glycol and propylene glycol, by reacting them with molybdenum metal and an organic hydroperoxide, peroxide, or $H_2O_2$. Molybdenum compounds prepared by reacting an ammonium-containing molybdate with a hydroxy compound, for example, an organic primary or secondary alcohol, a glycol or a phenol, are described in U.S. Pat. Nos. 3,784,482 and 3,787,329 to Cavitt.

U.S. Pat. No. 3,573,226 to Sorgenti discloses that molybdenum-containing epoxidation catalyst solutions may be made by heating molybdenum powder with a stream containing unreacted tertiary butyl hydroperoxide and polyhydric compounds of from about 200 to 300 molecular weight and having from 4 to 6 hydroxyl groups per molecule.

U.S. Pat. No. 3,953,362 to Lines, et al. reveals that novel molybdenum epoxidation catalysts may be prepared by reacting an oxygen-containing molybdenum compound with hydrogen peroxide and an amine and optionally water or an alkylene glycol at elevated temperatures. Similar catyasts are prepared by reacting an oxygen-containing molybdenum compound with an amine and an alkylene glycol at elevated temperatures according to Lines, et al. U.S. Pat. No. 4,009,122.

SUMMARY OF THE INVENTION

This invention is directed to the preparation of easily processed, storage stable solutions of molybdenum/alkanol complexes in the alkanol which are prepared by reacting an ammonium molybdate, preferably ammonium heptamolybdate tetrahydrate, with an amount of a straight chain or branched chain $C_6$–$C_{13}$ alkanol, preferably 2-ethyl-1-hexanol, within the range of about 7 to about 20 moles of alkanol per gram atom of molybdenum, the reaction being initiated in the presence of about 1 to 4 moles of added water per gram atom of molybdenum and conducted at a temperature of about 120° to about 190° C. for a period of time, normally about 3 to about 8 hours, sufficient to substantially completely remove ammonia and water to provide a liquid reaction product comprising said solution of molybdenum/alkanol complex dissolved in unreacted alkanol, and containing about 0.001 to about 0.1 wt. % of water. The reaction product is filtered to provide a clarified storage stable solution of the molybdenum/alkanol complex containing from about 4 to about 10.5 wt. % of dissolved molybdenum.

DETAILED DESCRIPTION OF THE PREFERRED EMBODIMENT

The improvements in the complexes of this invention relate to the discovery that the initial ratios of water, alcohol and ammonium molybdate, as well as reaction temperatures, have a significant effect on the amount of molybdenum that will be incorporated into the ammonium molybdate/alkanol catalyst complex as solubilized molybdenum, the ease of filterability of the finished reaction mixture and the stability of the finished complex solution with respect to staying clear and solids-free over the useful life of the catalyst.

The molybdenum compounds used to make the complexes of this invention are ammonium molybdates such as ammonium heptamolybdate tetrahydrate and ammonium dimolybdate.

It has been found that the ratio of alcohol to gram atoms of molybdenum and the ratio of water to gram atoms of molybdenum are important in determining the ease of processing of the complex during manufacture (reference to filtering after the digestion period), storage stability and the amount of molybdenum solubilized in the ammonium molybdate/alkanol complex.

The alcohols to be employed in the reaction to make the inventive complexes are primary straight chain or branched chain alkanols containing 6 to 13 carbon atoms, such as hexyl alcohol, octyl alcohol, decyl alcohol, tridecyl alcohol, isohexyl alcohol, isooctyl alcohol, etc. As is hereinafter explained in greater detail, the preferred alkanol is 2-ethyl-1-hexanol.

Thus, as shown by the working examples, 2-ethyl-1-hexanol can be processed with ease as compared with other commercially available alcohols such as hexyl, isooctyl, decyl and tridecyl alcohol. 2-Ethyl-1-hexanol is especially preferred because of its thermal stability and stability toward oxidation during the heating involved in preparing the catalyst (e.g., 3-8 hours at 175°-185° C.). Further 2-ethyl-1-hexanol imparts good filterability and storage stability to the complex.

Water and ammonia should be removed during the course of the reaction. The use of azeotroping agents with the alcohol/ammonium molybdate/water reactant system speeds the complex preparation by driving off water and ammonia. However, use of an azeotroping agent can lead to a certain random instability upon standing. Complexes made with this technique may be clear and solids free for days or weeks and then form solids seemingly all at once.

For the 2-ethyl-1-hexanol, ammonium heptamolybdate tetrahydrate, water system, the preferred reactant ratios are 7:1 to 13:1 expressed in terms of initial moles of alcohol to gram atoms of molybdenum in the molybdenum compound. An especially preferred range of moles of alcohol to gram atoms of molybdenum is 8.5:1 to 11.5:1. The reaction should be initiated in the presence of about 1 to 4 moles of added water per gram atom of molybdenum, in addition to the water of hydration of the molybdenum compound. The reaction temperature to make the inventive complexes should be between 120° and 190° C., preferably between 150° and 185° C., and the pressure should be atmospheric. Reaction temperatures of 175°-185° C. drive off the water and ammonia present in the reaction mixtures. Separation can be accomplished by filtration, centrifugation, decantation, sedimentation, etc.

The complexes and method of this invention are more particularly illustrated by the following examples which should not be construed as limiting the invention in any way. The examples also illustrate the use of the complexes of this invention as catalysts in an epoxidation reaction.

Complex Preparation

The following description of complex preparation is general for all preparations involving molybdenum 2-ethyl-1-hexanol complexes prepared from 2-ethyl-1-hexanol, ammonium heptamolybdate tetrahydrate, and added water, as noted.

The apparatus is a 1-liter Morton flask (round bottomed flask with 4 "flutes" or indentations in the bottom of the flask) fitted with a mechanical stirrer, nitrogen inlet, thermometer, Dean Stark trap and condenser, and a nitrogen exit via a bubbler containing mineral oil. The flask was heated using an electrical heating mantle and ordinary tap water was used in the condenser.

Procedure

To a flask equipped as described above was added ammonium heptamolybdate tetrahydrate (AHM) followed by 2-ethyl-1-hexanol (2E-HEX) and water. A slow nitrogen purge is established and the stirring and heat are turned on. In our small scale preparations in glassware, we normally heated with a rate such that the reaction mixture was taken from ambient temperature (20°-25° C.) to a reaction temperature (178°-185° C.) in 30-60 minutes. The heat up time is not critical, but once the reaction mixture reaches reflux the rate of heat input should be reduced to provide a steady reflux, but do not "over do" it. The reason for this is that after the reaction mixture reaches 178°-185° C., there is a 10-15 minute period before the evolution of ammonia begins at a good rate. During the heat up and the first 10-15 minutes some ammonia is being evolved but after 10-15 minutes at reflux the ammonia evolution increases. There is foaming due to the ammonia evolution and the flask or reaction vessel should be 3-4 times the volume of the reactants to insure that no bumping over or burping into the Dean Stark trap occurs. This is also one reason why the rate of heating is adjusted to achieve a steady reflux (necessary to drive off water and complete the reaction) but not to overdo the heat input because excessive foaming will occur. This ammonia evolution continues for 2-3 hours at a steady rate paralleling the rate of water removal via the Dean Stark trap. After completing the desired reaction period, usually 5-8 hours at essentially 178°-185° C. the reaction mixture is cooled and allowed to stand overnight, filtered and the filtrate stored under nitrogen. The solids collected are usually washed with acetone and dried. Weight of solids refers to these semi-washed and dried solids filtered from the cooled reaction mixture. Infrared spectroscopy and atomic absorption results (percent molybdenum) support identification of the solids as molybdenum trioxide.

The experimental results from complex preparations involving 2E-HEX, AHM and water are summarized in Table I. Table II summarizes typical propylene epoxidation results using certain of the molybdenum 2-ethyl-1-hexanol complexes described in Table I. Table III illustrates complex preparation from ammonium heptamolybdate and alcohols other than 2-ethyl-1-hexanol. These results were generally poorer than similar complex preparations with 2-ethyl-1-hexanol on the basis of percent molybdenum incorporated into the complex or in the ease of processing the complex. Utilizing optimum conditions described in this invention; namely 10:1 ratio of alcohol/g atoms of molybdenum and 2:1 mole ratio of water/g atoms of molybdenum, the absolute amount of molybdenum incorporated into the complex solution was generally more when the alcohol was 2E-HEX, as compared with the other alcohol, or the 2E-HEX samples were easier to process.

TABLE I

COMPLEX PREPARATIONS

Catalysts Made by Reacting Ammonium Heptamolybdate Tetrahydrate (AHM) and 2-Ethyl-1-Hexanol With and Without Water Present

| NB Run #[1] | Grams 2-Ethyl Hexanol | Grams AHM | Mole Ratio Alcohol/G.A. Moly | Gram Atoms Moly | Mole Ratio H₂O/G.A. Moly | Wt. % Moly in Cat. | % Moly Incorp into Cat. | % Moly Theory | Amt. S'ld | Ease of Filtration | Rxn Temp °C. | Rxn Time Hrs. | Wt. % N₂ in Cat. | Ml H₂O taken Ov'hd | Grams Filtrate Rec'd | Grs S'ld | Phy St. Days Cl'r |
|---|---|---|---|---|---|---|---|---|---|---|---|---|---|---|---|---|---|
| 5810-54 | 182.32 | 35.31 | 7.00/1 | 0.20000 | 0.0/1 | 10.30 | 96.90 | | Few | Fast | 178-181-171 | 5.0 | 0.02 | 16.5 | 180.5 | — | 7 C |
| 5810-56 | " | " | " | " | 1.5/1 | 10.30 | 99.69 | | Few | Fast | 177-181-171 | 5.0 | 0.51 | 22.5 | 185.7 | — | 20 C |
| 5855-4 | " | " | " | " | 2.0/1 | 9.79 | 92.20 | | Few | Fast | 177-181-168 | 8.0 | 0.42 | 24.5 | 180.7 | 3.0 | 60 C |
| 5810-60 | " | " | " | " | 3.5/1 | 10.10 | 92.80 | | Lot | Fast | 178-180-177 | 5.0 | 0.34 | 29.0 | 176.3 | — | 73 C |
| 5810-34 | 200.00 | 31.90 | 8.50/1 | 0.18067 | 0.0/1 | 8.04 | 87.41 | | Few | Fast | 180-181-174 | 5.0 | 0.05 | 14.0 | 188.4 | — | 13 C |
| 5855-5 | " | " | " | " | 1.538/1 | 8.82 | 102.17 | 8.63 | Few | Slow | 182-185-180 | 3.0 | 0.38 | 17.5 | 200.8 | 1.1 | 17 C |
| 5810-35 | " | " | " | " | 1.538/1 | 9.56 | 101.61 | 9.41 | Few | Fast | 182-183-181 | 5.0 | 0.14 | 16.5 | 184.2 | — | 13 C |
| 5855-8 | " | " | " | " | 2.0/1 | 8.33 | 94.67 | | Few | Fast | 176-180-167 | 5.0 | 0.39 | 23.2 | 197.0 | 0.9 | 35 C |
| 5810-36 | " | " | " | " | 3.075/1 | 7.76 | 86.64 | | Few | Fast | 178-180-174 | 8.0 | 0.44 | 24.0 | 193.5 | — | 12 C |
| 5810-37 | " | " | " | " | 4.612/1 | 8.17 | 89.57 | | Lot | Fast | 181-184-178 | 5.8 | 0.11 | 34.0 | 190.0 | — | 12 C |
| 5810-30 | 260.46 | 35.31 | 10.0/1 | 0.20000 | 0.0/1 | 4.54 | 58.67 | | Few | Slow | 178-180-169 | 5.5 | 0.04 | 17.0 | 247.7 | — | 1 C |
| 5855-10 | " | " | " | " | 1.0/1 | 7.41 | 99.91 | | Few | Fast | 178-179-168 | 6.0 | 0.40 | 22.0 | 258.7 | — | 9 C |
| 5855-12 | " | " | " | " | 1.5/1 | 7.59 | 101.74 | 7.46 | Few | Fast | 181-184-172 | 8.0 | 0.41 | 23.2 | 257.2 | 1.2 | 9 C |
| 5855-14 | " | " | " | " | 2.0/1 | 7.49 | 101.34 | 7.39 | Few | Fast | 177-180-168 | 8.0 | 0.35 | 25.3 | 259.6 | 1.5 | 13. C |
| 5855-15 | " | " | " | " | 2.5/1 | 7.20 | 100.38 | 7.17 | Few | Fast | 178-184-180 | 3.0 | 0.20 | 22.0 | 267.5 | — | 21 C |
| 5855-16 | " | " | " | " | 2.5/1 | 7.49 | 100.91 | 7.42 | Few | Fast | 180-184-172 | 8.0 | 0.40 | 27.0 | 258.5 | 1.0 | 50 C |
| 5855-18 | " | " | " | " | 3.0/1 | 7.11 | 96.75 | | Few | Fast | 178-180-168 | 8.0 | 0.39 | 29.0 | 261.6 | 1.3 | 49 C |
| 5810-49 | " | " | " | " | 3.5/1 | 6.58 | 86.83 | | Mod | Fast | 181-185-180 | 5.0 | 0.18 | 27.0 | 253.2 | — | 36 C |
| 5810-33 | " | " | " | " | 4.166/1 | 5.94 | 78.36 | | Mod | Slow | 178-182-180 | 5.0 | 0.25 | 31.0 | 253.1 | — | 14 C |
| 5780-90 | 299.5 | 35.50 | 11.4/1 | 0.20104 | 0.0/1 | 7.33 | 104.60 | 7.00 | Few | Mod | 178-180-179 | 5.0 | 0.31 | 12.5 | 275.4 | — | 20 C |
| 5810-50 | " | " | " | " | 1.1/1 | 6.59 | 103.00 | 6.40 | Few | Mod | 178-179-171 | 5.0 | 0.01 | 20.0 | 301.5 | — | 35 C |
| 5855-22 | " | " | " | " | 1.5/1 | 6.28 | 97.27 | | Few | Fast | 175-179-169 | 8.0 | 0.25 | 24.0 | 298.8 | 0.8 | 37 C |
| 5855-23 | " | " | " | " | 2.0/1 | 6.31 | 100.78 | 6.26 | Few | Fast | 178-180-176 | 3.0 | 0.28 | 21.0 | 308.1 | 0.9 | 30 C |
| 5780-95 | " | " | " | " | 2.764/1 | 6.16 | 94.65 | | Few | Fast | 180-180-178 | 5.0 | 0.23 | 24.0 | 296.4 | — | 16 C |
| 5810-53 | " | " | " | " | 4.0/1 | 5.55 | 83.00 | | Few | Mod | 181-184-180 | 5.0 | 0.04 | 28.0 | 288.5 | — | 34 C |
| 5780-99 | " | " | " | " | 5.527/1 | 4.50 | 64.25 | | Lot | Mod | 180-180-180 | 5.0 | 0.34 | 28.0 | 275.4 | — | 12 C |
| 5810-64 | 237.00 | 24.72 | 13.00/1 | 0.14000 | 0.0/1 | 5.63 | 92.92 | | Lot | Slow | 179-183-179 | 5.0 | 0.30 | 10.00 | 221.7 | N.D | 2 C |
| 5810-66 | " | " | " | " | 1.5/1 | 5.98 | 101.77 | 5.88 | Few | Fast | 181-184-179 | 5.0 | 0.30 | 13.5 | 228.6 | " | 43 C |
| 5810-69 | " | " | " | " | 3.0/1 | 5.81 | 101.30 | 5.74 | Few | Fast | 178-180-175 | 5.0 | 0.35 | 18.0 | 234.2 | " | 77 C |
| 5810-70 | " | " | " | " | 4.0/1 | 5.51 | 93.32 | | Lot | Fast | 180-184-180 | 5.0 | 0.29 | 19.5 | 227.5 | " | 55 C |
| 5855-66 | 299.5 | 35.50 | 11.4/1 | 0.20104 | 0.0/1 | 0.00 | 00.00 | | Lot | Mod | 99-101 | 14.5 | 1.39 | 0.0 | — | — | 36 C |
| 5740-22 | 169.3 | 20.08 | " | 0.11375 | 0.0/1 | 4.29 | 61.33 | | Lot | Mod | 150-160 | 3.5 | 0.29 | 0.7 | 156.0 | — | |

[1]The relationship of the runs to the examples in Table I of parent application S.N. 06/687,710 is as follows:
Example 10 = Run 5810-60; Example 11 = Run 5855-4; Example 12 = Run 5855-5; Example 13 = Run 5855-8; Example 14 = Run 5855-10; Example 15 = Run 5855-14; Example 16 = Run 3855-18; Example 17 = Run 5855-22; Example 18 = Run 5855-23 and Example 19 = Run 5810-69.

Turning now to Tables I and I-A, it will be noted that the experimental runs are arranged in the form of sets of data. In each "data set", the mole ratio of water to gram atoms of molybdenum is progressively increased from an initial run in which no water was added. When the "data sets" are compared it will be noted that good results were consistently obtained when the complex-forming reaction was conducted in the presence of about 1 to 4 moles of added water per gram atom of molybdenum and that erratic and less satisfactory results were obtained when the complex-forming reaction was conducted in the absence of added water or in the presence of an excessive amount of added water.

The last set of data (runs 5855-66 and 5740-22) are present to demonstrate the critical importance of temperature. Thus, run 5855-66, conducted at 99°-101° C., was a failure while excellent results were obtained in runs 5740-22 conducted at a temperature of 150°-160° C.

Turning now to the first five sets of data, and the first run of each set which was conducted in the absence of added water, it will be noted that in comparison with the other runs of each set of data, less than satisfactory results were obtained in respect of one or more of the following criteria:

weight percent of solubilized molybdenum in the catalyst complex,
percent of charged molybdenum incorporated into the catalyst,
amount of solids formed,
ease of filtration, and
physical state (number of days the catalyst complex remained clear.

Thus, in the first set of data, in run 5810-54, the catalyst complex remained clear for only 7 days. In the second set of data, in run 5810-34, storage stability (physical state, days clear) was low, the amount of charged molybdenum incorporated into the catalyst was low and the percentage of solubilized molybdenum was low, as compared with other runs in the second set of data. The same comment is in order for run 5810-30 of the third set of data and, in addition, a large quantity of solids were formed and the filtration rate was slow. The results for run 5780-90 of the fourth set of data were much better, but the filtration rate was moderate. In the fifth set of data, in run 5810-64, solids formation, ease of filtration and storage stability were unsatisfactory.

The same pattern can be observed for runs 5810-37, 5810-33 and 5780-99 where an excess of added water was used.

TABLE II

PROPYLENE EPOXIDATION RESULTS USING MOLYBDENUM 2-ETHYL-1-HEXANOL CATALYSTS DERIVED FROM AHM + 2-ETHYL HEXANOL
Results from Runs Using Low Propylene/TBHP Ratios, High TBHP Concentrations, Staged Temperatures and Variable Catalyst Levels

| Epox. Ex. | Cat. Used | Cat. Con. Wt. % Moly Basis Total Reaction Charge | TBHP, wt. % | Reaction Temp., °C. | Reaction Time, Hours | Propylene/ TBHP Mole Ratio | Product Analysis |||||
|---|---|---|---|---|---|---|---|---|---|---|---|
| | | | | | | | Propylene Oxide Wt. % | ppm $C_3$ dimer, pure PO basis (GC Mass Spec) | Propylene Oxide Yield | Propylene Oxide Selectivity | TBHP Conv. | Molybdenum Catalyst Recovery, % |
| 20 | 5810-60 | 0.0500 | 72.1 | 1110/135 | 1.0/1.05 | 1.22 | 31.95 | 16 | 97.40 | 99.76 | 97.63 | 78.5 |
| 21 | 5855-4 | 0.0256 | 72.6 | 110/135 | 1.0/1.0 | 1.12 | 31.56 | 16 | 93.37 | 96.14 | 97.12 | 94.1 |
| 22 | 5855-8 | 0.0251 | 72.6 | 110/136 | 1.0/1.0 | 1.14 | 31.79 | 10 | 94.48 | 98.11 | 96.30 | 96.3 |
| 23 | 5855-18 | 0.0251 | 72.6 | 110/136 | 1.0/1.0 | 1.14 | 31.79 | 10 | 94.48 | 98.66 | 95.76 | 89.0 |
| 24 | 5855-4 | 0.0197 | 72.6 | 110/140 | 1.0/1.0 | 1.14 | 31.70 | 14 | 94.12 | 97.91 | 96.13 | 98.2 |
| 25 | 5855-8 | 0.0201 | 72.6 | 110/140 | 1.0/1.0 | 1.12 | 32.45 | 13 | 93.05 | 97.43 | 95.51 | 99.5 |
| 26 | 5855-23 | 0.0198 | 72.6 | 110/141 | 1.0/1.0 | 1.14 | 31.18 | 13 | 92.68 | 96.91 | 95.63 | 93.7 |
| 27 | 5855-5 | 0.0199 | 72.6 | 110/140.8 | 1.0/1.0 | 1.13 | 31.80 | 13 | 94.25 | 98.48 | 95.71 | 89.7 |

TABLE III

COMPLEX PREPARATIONS
Alcohols From Exxon Chemical Americas + Ammonium Heptamolybdate + Water (150-190° C.)

| Example (Complex Preparation) | Alcohol | Reaction Time, Hours | Alcohol, grams | Ammonium Heptamolybdate, grams | Mole Ratio Alcohol/ g atoms Molybdenum |
|---|---|---|---|---|---|
| 1 | Hexyl | 6.0 | 102.0 | 25.22 | 7.0:1 |
| 2 | " | " | " | 20.77 | 8.5:1 |
| 3 | " | " | " | 17.66 | 10.0:1 |
| 4 | " | " | " | 15.45 | 11.4:1 |
| 5 | Isooctyl | 6.0 | 104.0 | 14.12 | 10.0:1 |
| 6 | " | " | " | 12.36 | 11.4:1 |
| 7 | " | " | " | 20.18 | 7.0:1 |
| 8 | " | " | " | 16.62 | 8.5:1 |
| 9 | " | " | " | 14.12 | 10.0:1 |
| 10 | " | " | " | 12.36 | 11.4:1 |
| 11 | Decyl | 6.0 | 102.7 | 16.39 | 7.0:1 |
| 12 | " | " | " | 13.50 | 8.5:1 |
| 13 | " | " | " | 11.48 | 10.0:1 |
| 14 | " | " | " | 10.04 | 11.4:1 |
| 15 | Tridecyl | 6.0 | 100.0 | 12.61 | 7.0:1 |
| 16 | " | " | " | 10.38 | 8.5:1 |
| 17 | " | " | " | 8.83 | 10.0:1 |
| 18 | " | " | " | 7.72 | 1.4:1 |

TABLE III-continued
COMPLEX PREPARATIONS
Alcohols From Exxon Chemical Americas +
Ammonium Heptamolybdate + Water (150–190° C.)

| | | | | | |
|---|---|---|---|---|---|
| 5855-4 | 2-Ethyl-1-hexanol | 8.0 | 182.32 | 35.31 | 7.0:1 |
| 5855-8 | " | " | 200.00 | 31.90 | 8.5:1 |
| 46 | " | " | 260.46 | 35.31 | 10.0:1 |
| 47 | " | " | 260.46 | 35.31 | 10.0:1 |
| 5855-23 | " | 3.0 | 299.5 | 35.50 | 11.4:1 |

| Example (Complex Preparation) | Mole Ratio Water/ g atoms Molybdenum | Molybdenum in Complex, Wt. % | Molybdenum Incorporated, % | Amount of Solids to Filter | Ease of Filterability | Days Complex Stayed Clear |
|---|---|---|---|---|---|---|
| 1 | 2.0:1 | 13.20 | 58.08 | Lot | V. Slow | 0 |
| 2 | " | 11.00 | 89.66 | Mod. | Slow | 1 |
| 3 | " | 9.80 | 93.75 | Mod. | Slow | >29 |
| 4 | " | 8.64 | 101.47 | Mod. | V. Slow | 17 |
| 5 | 0.0:1 | 6.89 | 88.09 | Few | Slow | 17 |
| 6 | 0.0:1 | 5.59 | 83.48 | Few | Slow | 17 |
| 7 | 2.0:1 | 11.00 | 105.33 | Trace | Fast | 1 |
| 8 | " | 8.87 | 103.62 | Few | Fast | 1 |
| 9 | " | 6.56 | 85.58 | Few | Fast | 15 |
| 10 | " | 5.60 | 84.63 | Few | Fast | 23 |
| 11 | 2.0:1 | 2.95 | 31.17 | Lot | Mod. | >38 |
| 12 | " | 6.19 | 78.98 | Few | Slow | 2 |
| 13 | " | 6.01 | 97.31 | Few | Fast | 1 |
| 14 | " | 5.17 | 95.52 | Few | Mod. | 1 |
| 15 | 2.0:1 | 6.43 | 94.78 | Few | Slow | 1 |
| 16 | " | 5.03 | 84.98 | Few | Slow | 1 |
| 17 | " | 4.77 | 97.40 | Few | Fast | >43 |
| 18 | " | 3.44 | 81.18 | Mod. | Slow | >43 |
| 5855-4 | 2.0:1 | 9.79 | 92.20 | Few | Fast | >19 |
| 5855-8 | 2.0:1 | 8.33 | 94.67 | Few | Fast | >8 |
| 46 | 1.5:1 | 7.59 | 101.74 | Few | Fast | 9 |
| 47 | 2.5:1 | 7.49 | 100.91 | Few | Fast | >23 |
| 5855-23 | 2.0:1 | 6.31 | 100.78 | Few | Fast | >11 |

Many modifications may be made by one skilled in the art in this invention without changing the spirit and scope thereof which are defined only in the appended claims. The complexes of this invention have a high molybdenum content, are stable upon standing and are easily filterable, and provide excellent epoxidation results.

We claim:

1. A method of preparing a storage stable solution of a catalytically active complex of molybdenum with a primary straight chain or branched chain alkanol containing 6 to 13 carbon atoms in said alkanol which comprises:
   reacting an ammonium molybdate with said alkanol in the presence of water, within the range of about 7 to about 20 mols of alkanol per gram atom of molybdenum sufficient to form a storage stable molybdenum/alkanol complex, said reaction being initiated in the presence of about 1 to about 4 mols of water per gram atom of molybdenum, said reaction being continued at atmospheric pressure at a temperature of about 120° to about 190° C. for a period of time with the range of about 3 to about 8 hours sufficient to substantially completely remove ammonia and water and to provide a liquid reaction product having said molybdenum/alkanol complex dissolved in unreacted alkanol and about 0.001 to about 0.1 wt. % of water,
   and recovering a clarified, storage stable solution of said catalytically active molybdenum/alkanol complex in said alkanol, and containing from about 4 to about 10.5 wt. % of dissolved molybdenum.

2. A method as in claim 1 wherein the mole ratio of alkanol to gram atoms of molybdenum is within the range of about 8.5 to about 15 and the reaction temperature is within the range of about 150° to about 185° C.

3. A method as in claim 2 wherein the alkanol is a hexyl alcohol.

4. A method as in claim 2 wherein the alkanol is iosoctyl alcohol.

5. A method as in claim 2 wherein the alkanol is decyl alcohol.

6. A method as in claim 2 wherein the alkanol is tridecyl alcohol.

7. A method of preparing a storage stable solution of a catalytically active complex of molybdenum with 2-ethyl hexanol in 2-ethyl hexanol which comprises:
   reacting ammonium heptamolybdate tetrahyderate with 2-ethyl hexanol in amount within the range of from about 7 to about 20 mols of said 2-ethyl hexanol per gram atom of molybdenum; said reaction being initiated in the presence of about 1 to about 4 mols of water per gram atom of molybdenum said reaction being continued at atmospheric pressure at a temperature of about 120° to about 190° C. for a period of time within the range of about 3 to about 8 hours sufficient to substantially completely remove ammonia and water and to provide a liquid reaction product comprising said molybdenum/2-ethylhexanol complex dissolved in 2-ethyl hexanol and containing about 0.001 to about 0.1 wt. % of water, and
   recovering a clarified, storage stable solution of said catalytically active molybdenum/2-ethyl hexanol complex in 2-ethyl hexanol, and containing about 4 to about 10.5 wt. % of dissolved molybdenum.

8. A method as in claim 7 wherein the 2-ethyl-1-hexanol is present in an amount sufficient to provide a mole ratio of about 8.5 to about 15 moles of 2-ethyl-1-hexanol per gram atom of molybdenum.

9. A method as in claim 8 wherein the temperature is within the range of about 150° to about 185° C.

10. A method as in claim 8 wherein the temperature is within the range of about 175° to about 185° C.

* * * * *